(12) United States Patent
Arkles et al.

(10) Patent No.: US 6,800,777 B2
(45) Date of Patent: Oct. 5, 2004

(54) TRIALKYLSILANES FOR USE IN CHROMATOGRAPHIC APPLICATIONS, SUBSTRATES INCLUDING SUCH COMPOUNDS AND METHODS OF PRODUCING THE SAME

(75) Inventors: Barry C. Arkles, Dresher, PA (US); Gerald L. Larson, Newtown, PA (US); Youlin Pan, Langhorne, PA (US)

(73) Assignee: Gelest, Inc., Morrisville, PA (US)

( * ) Notice: Subject to any disclaimer, the term of this patent is extended or adjusted under 35 U.S.C. 154(b) by 0 days.

(21) Appl. No.: 10/138,746

(22) Filed: May 3, 2002

(65) Prior Publication Data

US 2002/0173670 A1 Nov. 21, 2002

Related U.S. Application Data

(60) Provisional application No. 60/288,302, filed on May 3, 2001.

(51) Int. Cl.[7] .................................................. C07F 7/02
(52) U.S. Cl. ...................... 556/400; 556/430; 556/450; 556/465; 556/489
(58) Field of Search ................................ 556/400, 430, 556/450, 465, 489

(56) References Cited

U.S. PATENT DOCUMENTS

| | | | |
|---|---|---|---|
| 5,453,528 A | * | 9/1995 | Boutevin et al. ........... 556/431 |
| 5,710,301 A | | 1/1998 | Fujiki |
| 5,874,603 A | | 2/1999 | Arkles |
| 6,071,410 A | | 6/2000 | Nau et al. |

FOREIGN PATENT DOCUMENTS

EP  0 579 102 B1  9/1997

OTHER PUBLICATIONS

Kan et al, Polymers for dvanced Technologies, vol. 7, pp 76–78, 1994.*
O'Gara et al., "Systematic Study of Chromatographic Behavior vs Alkyl Chain Length for HPLC Bonded Phases Containing an Embedded Carbamate Group," *Anal. Chem.*, vol. 71, No. 15, pp. 2992–2997 (Aug. 1, 1999).
Horváth, "Reverse Phase Chromatography with Alkyl–Silica Stationary Phases," *Silylated Surfaces*, D.E. Leyden, W. Collins, pp. 269–300 (1980).
Wise et al., "Investigations Of Selectivity In Reversed–Phase Liquid Chromatography On Chemically Bonded C18 Phases," *Silanes Surfaces Interfaces*, D.E. Leyden et al., pp. 349–370 (1986).
Van Der Voort et al,. "Silylation of the silica Surface A Review," *J. Liq. Chrom. & Rel. Technol.*, vol. 19, Nos. 17 & 18, pp. 2723–2752 (1996).
Purdy, et al. "Synthesis of High–Dielectric, Crosslinked Silicone Materials," Polymeric Materials: Science & Engineering, vol. 84, pp. 641–642 (2001).

* cited by examiner

*Primary Examiner*—Shailendra Kumar
(74) *Attorney, Agent, or Firm*—Akin Gump Strauss Hauer & Feld, LLP

(57) ABSTRACT

The invention includes a trialkylsilane comprising a hydrocarbon backbone including one to ten carbon atoms; a terminal trialkylsilyl moiety having at least two alkyl groups independently comprising at least six carbon atoms; and a terminal silyl moiety that has at least one hydrolyzable group bound to a silicon of the silyl moiety. At least one of the alkyl groups of the trialkylsilyl moiety may substituted with at least one halogen, and is preferably a perfluoroalkyl group. The invention also provides methods of producing the trialysilane and substrates including the trialkysilane of the invention, as well as columns and substrates for use in chromatographic applications.

10 Claims, 5 Drawing Sheets

FIGURE 1. Alkyl Chain Folding
CHAIN FOLDING
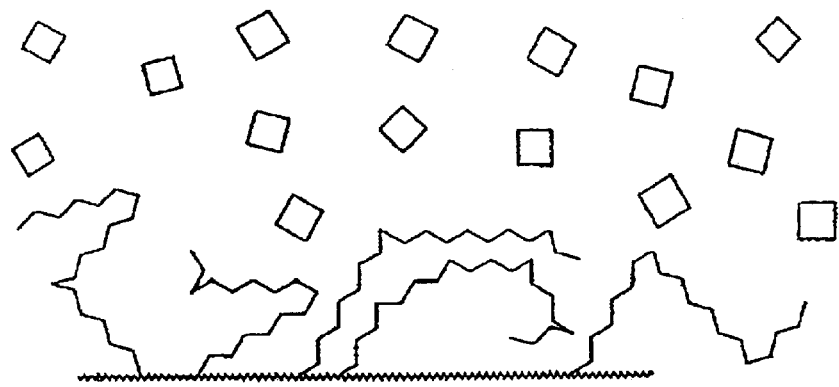
SILICA SURFACE
☐ = POLAR (AQUEOUS) SOLVENT MOLECULE
REGENERATED
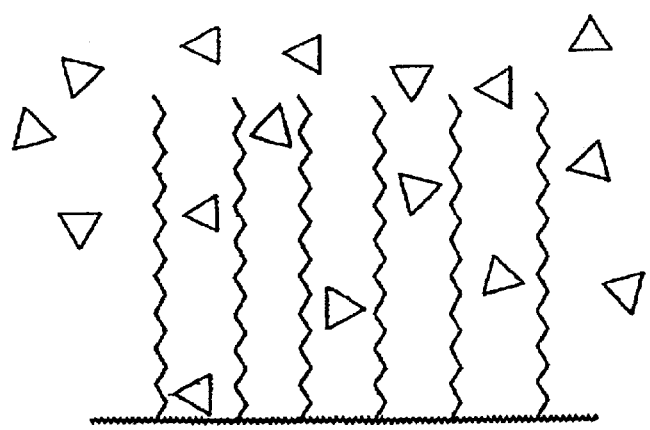
SILICA SURFACE
△ = NON-POLAR ORGANIC SOLVENT MOLECULE

FIGURE 2. Polar Embedded Groups
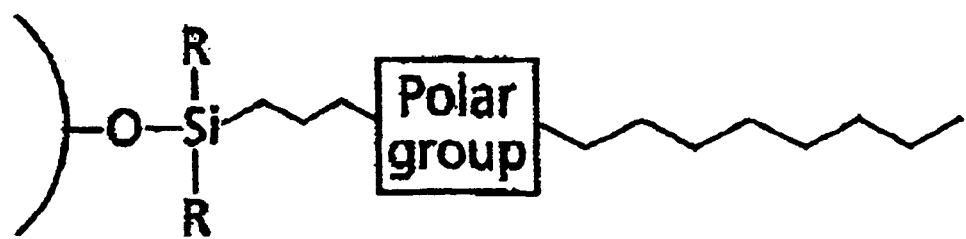
Polar Group
Amide     —CONHR
Ether     —O—
Ester     —COOR

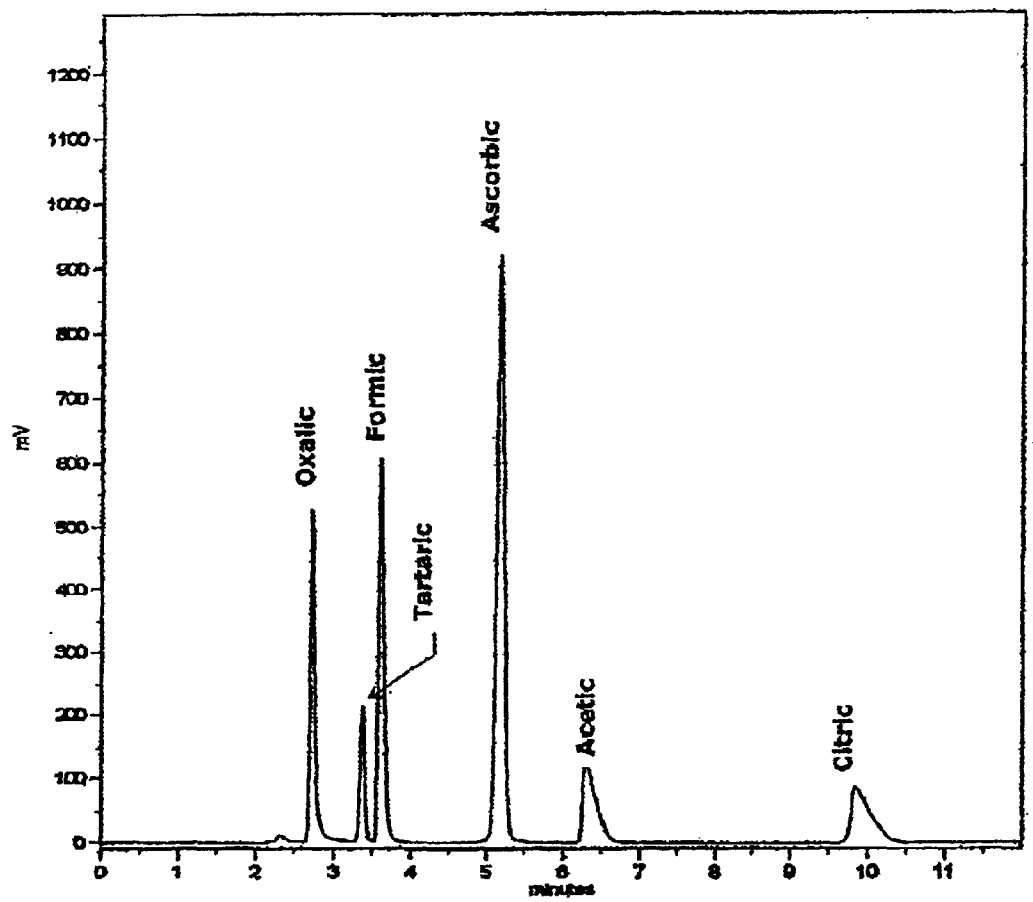
FIGURE 3. SEPARATION OF ALKYL CARBOXYLIC ACIDS ON DI-N-DODECYLMETHYLSILYLETHYL BONDED SILICA, 250x4.6mm, 60Å, 5μA.

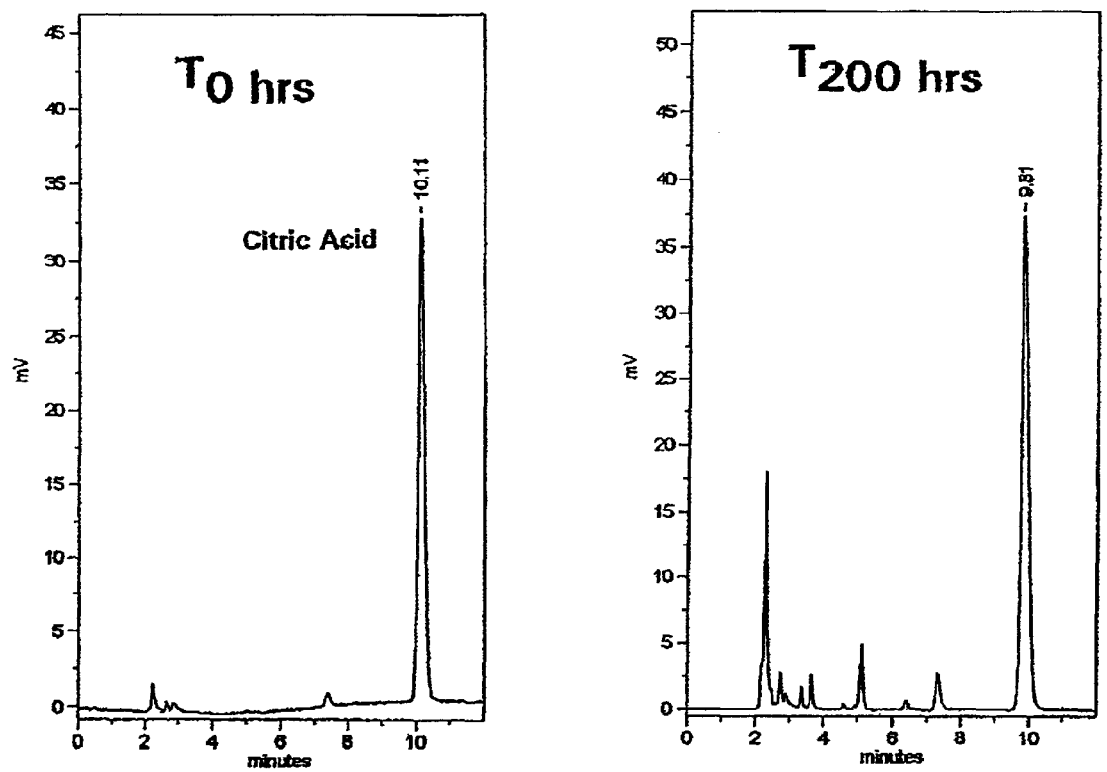
FIGURE 4. RETENTION TIME STABILITY OF CITRIC ACID ON DI-DODECYLMETHYLSILYLETHYL BONDED SILICA, 250 x 4.6 mm, 60A, 5u FIGURE 5. RETENTION TIME INSTABILITY OF CARBOXYLIC ACIDS ON CONVENTIONAL C18 BONDED SILICA, 250 x 4.6 mm, 60A, 5u
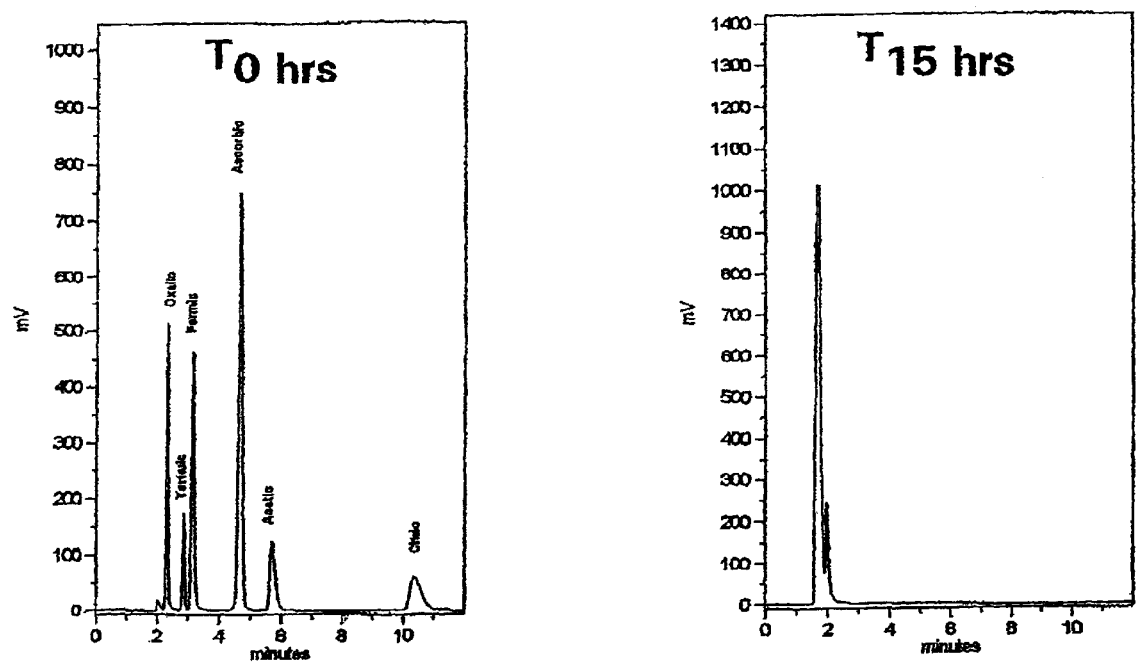

TRIALKYLSILANES FOR USE IN CHROMATOGRAPHIC APPLICATIONS, SUBSTRATES INCLUDING SUCH COMPOUNDS AND METHODS OF PRODUCING THE SAME

CROSS-REFERENCE TO RELATED APPLICATIONS

This application claims the benefit under 35 U.S.C. § 119(e) of U.S. Provisional Patent Application No. 60/288,302, filed May 3, 2001, the contents of which are incorporated herein by reference.

BACKGROUND OF THE INVENTION

Liquid phase chromatography and extraction techniques are dependent upon the interaction of a region bonded to a solid support, such as silica, with a solvent environment containing the solute or solutes of interest. In such applications, the solid support is stationary relative to the liquid or solvent phase. The "interacting region" where the region bonded to the solid support and the solvent environment interact is commonly known as the "bonded phase" or "interphase." A general overview of technology relating to chromatographic applications may be found in, for example, C. Horvath, *Silylated Surfaces* (1980).

A useful, successful bonded phase is characterized by reproducible, non-binding interactions with solutes in the mobile phase under a variety of chromatographic operating conditions, including conditions of temperature and pressure, and conditions relating to the nature of the solvent used and the stability of the interaction over a period of time.

Liquid phase chromatography has numerous industrial, clinical, and research applications. Recently, there has been much interest in liquid chromatographic separations of polar analytes, such as carboxylic acids, nucleic acids, and other polar molecules. To achieve adequate retention and separation of many of these polar analyte compounds on alkyl bonded phase supports, it is necessary to employ straight aqueous mobile phases.

Use of conventional bonded phases such as the widely used octadecyl ("C18") phase while employing straight aqueous mobile phases results in separations and analyte retentions that are initially satisfactory. However, after a few hours of contact with the straight aqueous mobile phase, the conventional bonded phase column typically exhibits loss of separation and of analyte retentions. This significantly reduces the accuracy and efficiency of chromatographic analysis.

It is conventionally considered that these observed phenomena are attributable to a "folding" process of the C18 ligand in the straight aqueous environment, sometimes referred to as "phase collapse." A schematic representation of the "folding" phenomenon of the C18 ligand is illustrated in FIG. 1. It is believed that the folding phenomenon occurs because the straight alkyl C18 chain is at a higher thermodynamic energy state in the straight aqueous environment relative to it energy state in an aqueous/organic environment (e.g., water/acetonitrile). When the alkyl ligand undergoes folding, the hydrophobic region available for interaction with the polar analytes decreases in size, and a commensurate loss of analyte retention is observed. It is conventional practice to "re-extend" the folded alkyl chains by passing a small amount of a polar solvent, such as methanol, through the C18 column. The analyte retentions will then return to their initial values after a short equilibration with the straight aqueous mobile phase. However, this remedy is transient; after a period of time, the analyte retentions will again decrease as a function of the C18 chain folding and the re-extending process must be repeated.

Prior art efforts to eliminate or minimize the previously described folding phenomenon with C18 columns employing straight aqueous mobile phases include use, in the bonded phase, of molecules employing "polar embedded groups" at some position in the alkyl chain. For example, a schematic representation of a polar embedded group in an alkyl chain is provided in FIG. 2. Groups conventionally considered useful as polar embedded groups include amides, esters, and ethers. The polar embedded groups serve to facilitate the wetting of the hydrocarbon (C18) chain and thereby minimize the folding phenomenon. A disadvantage of this approach is that the system is often unstable when mobile phases of low pH values (e.g., pH 2–3) are used, and in some cases, the system exhibits unfavorable analyte selectivities.

Additionally, branched alkylsilanes having a branched hydrocarbon backbone with branched alkylsilane moieties extending asymmetrically from the backbone also exhibit minimal phase collapse when used as a bonded phase in chromatographic and separation applications. Such branched alkylsilanes are disclosed in U.S. Pat. No. 5,874,603, issued Feb. 23, 1999.

Accordingly, there is a need in the art for a material for forming an improved bonded phase that exhibits the increased bonded phase interaction of C18 and good retention characteristics over time, while minimizing the effect of chain folding (phase collapse) in straight aqueous mobile phases. Further, there is a need for a simple synthesis reaction for forming a trialkylsilane having a relatively long chain length with a high level of purity for use in a bonded phase.

BRIEF SUMMARY OF THE INVENTION

The invention is a trialkylsilane comprising a hydrocarbon backbone including one to ten carbon atoms; a terminal trialkylsilyl moiety on the backbone having at least two alkyl groups independently comprising at least six carbon atoms; and a terminal silyl moiety on the backbone that has at least one hydrolyzable group bound to a silicon of the silyl moiety. At least one of the alkyl groups of the trialkylsilyl moiety may be substituted, preferable with at least one halogen. Most preferably, at least one of the alkyl groups of the trialkylsilyl moiety is a perfluoroalkyl group. Additionally, the invention is a trialkylsilane represented by the formula (I);

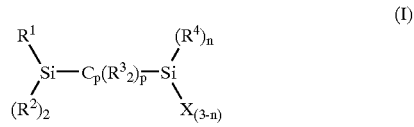

wherein $R^1$ is a linear or branched alkyl chain of one to four carbon atoms; $R^2$ is independently selected from a substituted, unsubstituted linear or branched alkyl chain having m carbons, where m is an integer such that $6 \leq m \leq 18$; $R^3$ is independently a hydrogen atom, or a branched or linear, substituted or unsubstituted alkyl group; p is an integer of one to ten; $R^4$ is a linear or branched alkyl group of one to four carbon atoms or an aryl group; n is an integer of zero to two; and x is a hydrolyzable group.

The invention also encompasses a treated substrate for use in chromatographic applications. The treated substrate includes a substrate and the trialkylsilane of the invention.

Further contemplated within the scope of the invention is a method for preparing the trialkylsilane for use in chromatographic applications. The method includes preparing a disubstituted vinylsilane by reacting an organomagesium reagent and an alkyl vinylfunctionalsilane or an aryl vinylfunctionalsilane to obtain a disubstituted alkylvinylsilane or a disubstituted arylvinylsilane; reacting the disubstituted vinylsilane of step (a) in a monomeric silane containing a silicon-hydrogen bond in the presence of a metallic catalyst. The monomeric silane is added to the vinyl group of the vinylsilane, thereby binding the silicon of the monomeric silane to the terminal carbon of the vinyl group and forming a trialkylsilane having a terminal trialkylsilyl moiety wherein at least two alkyl groups of the trialkylsilyl moiety independently comprise at least six carbon atoms and the least two alkyl groups extend from the silicon of the prepared vinylsilane.

Also described herein is a method for forming a bonded phase for use in chromatographic applications. The method includes forming a trialkylsilane which comprises a hydrocarbon backbone having one to ten carbon atoms, a terminal trialkylsilyl moiety (having at least two alkyl groups independently comprising six to eighteen carbon atoms) on the hydrocarbon backbone, a terminal silyl moiety on the backbone wherein the silicon of the silyl moiety is capable of being bound to a substrate, and reacting the trialkylsilane with a substrate comprising silicon in the presence of a hydroxy-containing compound to form an Si—O—Si bond between the silicon of the silyl moiety and the silicon of the substrate, such that the at least two alkyl groups of the trialkylsilyl moiety extend to provide a bonded phase useful for reproducible molecular interaction.

The invention also includes a column for use in chromatographic applications. The column includes a treated substrate that contains the trialkylsilane of the invention.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments that are presently preferred. It should be understood, however, that the invention is not limited to the precise arrangements and instrumentalities shown.

In the drawings:

FIG. 1 is a schematic representation of the phenomenon of chain folding exhibited by prior art bonded phases;

FIG. 2 is schematic representation of a conventional C18 chain having a polar embedded group;

FIG. 3 is a chromatograph showing separation of alkyl carboxylic acids on a column prepared in accordance with the invention;

FIG. 4 is a chromatograph showing retention stability of citric acid on a column prepared in accordance with the invention; and FIG. 5 is a chromatograph showing retention time instability of a column prepared using a prior art material.

DETAILED DESCRIPTION OF THE INVENTION

The invention described is a trialkylsilane, having a trialkylsilyl moiety which includes at least two alkyl groups that extend to provide a bonded phase useful for reproducible molecular interaction. Also described is a treated substrate for use in chromatographic applications including a substrate and the trialkylsilane of the invention, a method of preparing the trialkylsilane, a method for forming the bonded phase, and a column including the substrate of the invention. The bonded phase that is formed using the trialkylsilane of the invention has increased bonded phase interaction capacity of the conventionally used bonded phase compounds, but exhibits minimal folding in straight aqueous mobile phases and stable retention characteristics, thereby providing a bonded phase suitable for applications involving the separation of polar analytes, such as nucleic acids, certain proteins, and carboxylic acids.

As used in the context of this specification, "branched" refers to any molecule other than a straight chain molecule. "Aliphatic" refers to an organic compound that does not contain an aromatic ring. "Aromatic" is used herein to describe an organic compound containing a benzene or a benzene-derived ring having a resonance structure.

"Hydrolyzable" describes a compound or group capable of being hydrolyzed in the presence of water or an —OH species. As used herein, "substituted" means an organic or hydrocarbon structure in which one or more of the bonds or atoms is replaced by a substituent group, such as a linear or branched functional group, alkyl groups, ionic groups, and the like.

The description provided herein details several embodiments of the invention; however, it should be understood that the invention is not limited to the embodiments described.

The invention includes a trialkylsilane compound, monomeric in nature, that has a primary hydrocarbon backbone of one to ten carbon atoms. The backbone, however, preferably contains one to five carbon atoms, and most preferably contains two carbon atoms. The backbone is preferably aliphatic, although aromatic groups may be included in the backbone chain. The backbone may be substituted or unsubstituted; if substituted, various functional groups useful in specific applications may be incorporated, such as those useful in the separation of polar analytes, as long as the primary hydrocarbon backbone maintains a substantially linear character and the relative location of the silyl moiety and of the trialkylsilyl moiety is maintained as described herein. Functional groups can include, for example, halogen groups, alkyl groups, alkoxy groups, amine or amide groups, etc.

The backbone of the trialkylsilane described herein has two terminal ends. While there may be other "terminal" groups of the trialkylsilane if it is branched, it is the two terminal end group of the backbone referred to herein. At the first terminal end, there is a trialkylsilyl moiety. The three alkyl groups attached to the silicon of the trialkylsilyl moiety may each independently be branched, linear, substituted, or unsubstituted. It is preferred that at least one, preferably at least two, of the alkyl groups attached to the trialkylsilyl moiety is substituted, preferably by halogens, with the preferred halogen being fluorine. For example, at least one, preferably two, of the alkyl groups may be a perfluoroalkyl group, especially if the resulting trialkylsilane is to be used in reverse-phase separation of proteins. See, for example, Geng et al., J. Chromatography, 1983, 269, pages 96–102.

At least two of these alkyl groups independently include at least six carbon atoms, and preferably ten to eighteen carbon atoms, and most preferably twelve to fourteen carbons atoms. It is preferred that these at least two alkyl groups are aliphatic (straight chain), but they may be wholly or partially substituted, preferably with halogens, most preferably with fluorine atoms.

Additionally, the trialkylsilyl moiety of the first terminal end may include a linear or branched, substituted, or unsubstituted alkyl group having one to four carbon atoms. Preferably, this alkyl group is a methyl group.

At the second terminal end of the backbone is a terminal silyl moiety that has at least one hydrolyzable group bound to the silicon of the silyl moiety. If greater than one hydrolyzable group is present, the groups may be the same, or they may be different from one another. The hydrolyzable of the silyl moiety should be capable of reacting with a given substrate for use in chromatographic applications. Accordingly, the hydrolyzable groups may be varied or functionalized for use with a selected, specific substrate, which will usually be application specific, and may be any substrate known or developed in the art. Preferred substrates to which the hydrolyzable group can be bound include, for example, mullite, zirconia, silica, and titania.

If the trialkylsilane is to be used in an HPLC application, the preferred substrate will likely include silica. Hydrolyzable groups for use in the present invention if a silica-containing substrate is used, include may include, without limitation, halogens, such as, for example, chlorine, fluorine, bromine, and iodine; alkylamines and dialkylamines, such as, for example, methylamine, ethylamine, propylamine, isopropylamine, butylamine, isobutylamine, pentylamine, hexylamine, dimethylamine, diethylamine, methylethylamine, dipropylamine, methylpropylamine, ethylpropylamine, and similar compounds; and alkoxy groups, such as, for example, methoxy, ethoxy, propoxy, isopropoxy, butoxy, and the like. Preferably, the hydrolyzable group(s) is a chlorine atom, an alkylamine, a dialkylamine or an alkoxy group, such as methoxy or ethyoxy. However, other hydrolyzable groups having similar properties may be used, or other groups may be selected for reactions with non-silicon-containing substrates, as is known or to be developed in the art.

If the terminal silyl moiety of the second terminal end contains only one hydrolyzable group, the moiety can additionally contain at least one linear or branched, substituted or unsubstituted alkyl chain of one to four carbon atoms or an aryl group.

The trialkylsilane, as described above, preferably has the following formula (I):

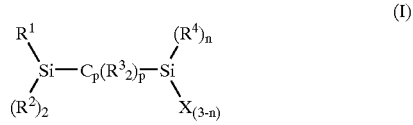

(I)

wherein $R^1$ is a linear or branched alkyl chain of one to four carbon atoms; $R^2$ can be substituted or unsubstituted, linear or branched alkyl chains or halogenated alkyl chains having m carbon atoms, where m is an integer such that $6 \leq m \leq 18$; $R^3$ is independently a hydrogen atom, or a substituted or unsubstituted linear or branched alkyl group or an aromatic group; p is an integer of one to ten, although it is preferred that p is two; $R^4$ is a linear or branched substituted or unsubstituted alkyl group of one to four carbon atoms or an aryl group; n is an integer of zero to two, with zero being preferred; and X is a hydrolyzable group that is preferably independently selected from the group consisting of a halogen, an alkyl amine group, a dialkylamine group, and alkoxy group.

Preferably, R1 is a substituted or unsubstituted methyl group. It is preferred that $R^2$ is an alkyl chain having ten to eighteen carbon atoms ($10 \leq m \leq 18$) or, most preferred, twelve to fourteen carbons atoms ($12 \leq m \leq 14$). $R^2$ may each be independently partially or wholly substituted, preferably with halogens. Preferably, $R^2$ is substituted with at least one halogen, with the halogen preferably being a fluorine atom. Most preferably, if substituted, $R^2$ may be independently selected from perfluoroalkyl chains. In another preferred embodiment, $R^2$ is —$R^f$ $CH_2CH_2$, where $R^f$ is independently selected from $C_6(P^x)_{13}$ $CH_2CH_2$—, $C_8(P^x)_{17}$ $CH_2CH_2$—, or $C_{10}(P^x)_{21}$ $CH_2CH_2$—, and $P^x$ is a halogen, preferably fluorine.

The trialkylsilane as described above, and preferably as represented by formula (I), may be formed by any acceptable chemical reaction pathway; however, it is preferred that the trialkylsilane is formed by the incorporation of an alkyl group onto an appropriate vinylsilane, followed by hydrosilylation of the resultant disubstituted vinylsilane to give a single isomeric product that can be bonded to a substrate, for example, silica. As illustration, formation by a hydrosilylation reaction of a vinylsilane and a monomeric silane can be employed. The hydrosilylation may be accomplished by free radical initiation brought about by heat, peroxides, or irradiation; however, it is preferred that the hydrosilylation is carried out in the presence of a metallic catalyst, as discussed infra.

In a particular embodiment, production of the trialkylsilane of the invention involves, first, preparation of an initial disubstituted vinylsilane. This can be achieved, for example, by reacting an organometallic reagent and an alkyl vinylfunctionalsilane or an aryl vinylfunctionalsilane.

The vinylfunctional silanes, e.g., the alkyl vinylfunctional silanes or aryl vinylfunctional silanes, for reaction with the organometallic reagent may be any known or developed in the art, and may contain any functional group as is known or developed in the art, depending on the specific chromatographic or separation application for which the end product trialkylsilane is to be used. Preferred functional groups are halogens, such as chlorine and, most preferably, fluorine.

The organometallic reagent for use in the preparation of the disubstituted vinylsilane can include any organometallic reagent known in the art, although preferred are organomagnesium reagents such as, for example, those having the formula $R^5MgY$, where $R^5$ is a linear or branched, substituted, or unsubstituted alkyl group having six to eighteen carbon atoms, preferably ten to eighteen carbon atoms, and Y is a halogen, such as, for example, bromine.

The synthesis of the disubstituted alkyl vinylsilane or disubstituted aryl vinylsilane for use in the methods of the invention may follow the reaction (II):

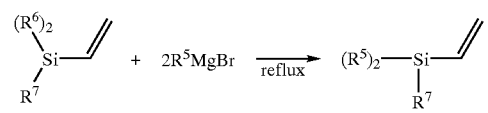

wherein $R^5$ is independently a linear or branched substituted or unsubstituted alkyl group having six to eighteen carbon atoms, preferably ten to eighteen, $R^6$ is a halogen group (independently selected or the same), $R^7$ is an alkyl group, substituted, unsubstituted, linear or branched, having one to four carbon atoms. Preferably, $R^7$ is a methyl group.

After the disubstituted vinylsilane as described above is prepared, it can then be used in, for example, a hydrosilation reaction to arrive at the trialkylsilane of the invention.

Monomeric silane(s) for use in the hydrosilation reaction with the disubstituted vinylsilane may be a silane or an alkyl silane having at least one silicon atom. Preferably the silicon atom is bound to a hydrogen atom. Other functional groups, substituted groups, and hydrolyzable groups may also be bound to the silicon of the monomeric silane. The monomeric silane can have the following formula (III):

$$(R^8)_3SiH \quad (III)$$

wherein $R^8$ is independently a hydrolyzable group, such as, for example, a halogen, preferably chlorine; alkyl amines, preferably dimethylamine and diethylamine; and alkoxy groups, such as, for example, methoxy, ethoxy, propoxy, isopropoxy, butoxy, and the like, with ethoxy being preferred.

It is preferred that the monomeric silane has the formula $(R^4)_nSiX_{(3-n)}$, where $R^4$ is a linear or branched substituted or unsubstituted alkyl group of one to four carbon atoms or an aryl group (preferably a methyl group or a phenyl group); n is an integer of zero to two; and X is a hydrolyzable group that may be independently selected from the group consisting of a halogen, an alkyl amine group, a dialkylamine group, and alkoxy group, as described above.

The monomeric silane contains a silicon-hydrogen bond. In the hydrosilation reaction, the disubstituted vinylsilane is reacted with the monomeric silane in the presence of a metallic catalyst, such that the silane is added to the vinyl group of the disubstituted vinylsilane, thereby converting the vinyl double bond to a single bond, and bonding the silicon of the monomeric silane to the terminal carbon of the vinyl group, thereby forming a trialkylsilane having two separate long-chain hydrocarbon groups extending from the silicon atom of the disubstituted vinylsilane.

The hydrosilation reaction may be accomplished as follows, in the presence of a metallic catalyst (IV):

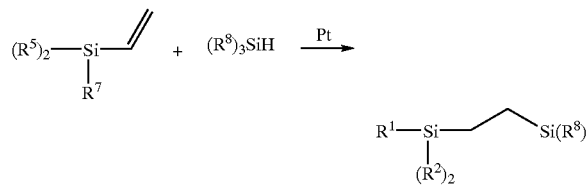

wherein $R^5$ and $R^2$ are each independently a linear or branched, substituted or unsubstituted alkyl group having six to eighteen carbon atoms, preferably ten to eighteen; $R^7$ and $R^1$ are an alkyl group or a halogenated alkyl group, either of which may be substituted, unsubstituted, linear or branched, having one to four carbon atoms; and $R^8$ is independently a hydrolyzable group as described supra. "Pt," as used above, represents a metallic catalyst, as discussed infra.

Metallic catalysts which may be used to facilitate this hydrosilylation reaction include platinum complex catalysts, such as, for example, platinum-divinyltetramethyldisiloxane complex, platinum-cyclovinyl methylsiloxane complex, platinum-tetramethyldisiloxane complex, chloroplatinic acid, chloroplatinic acid complexes and/or solutions, and tris-triphenyl phosphine rhodium chloride. More preferable, the hydrosilylation catalyst is platinum-divinyltetramethyldisiloxane complex.

The reaction represented by formula IV may be carried out with an excess (preferably about a 10% excess) of the monomeric alkylsilanes; however this is not necessary. All, or optionally only a portion, of the monomeric alkylsilane is initially added to the disubstituted alkyl or aryl vinylsilane, which is preferably in a liquid medium, or more preferably, in a solvent medium. The metallic catalyst may be charged to the reaction mixture. The reaction mixture should then be heated to a temperature of from about 30° C. to 200° C., preferably from about 60° C. to about 160° C. It is preferred that the heating takes place under substantially oxygen-free conditions. An exotherm, typically moderate, may occur, at which time, the remaining amount of alkylsilane monomer, if not already added, may be added to the reaction mixture, while maintaining the temperature in the range dated above.

If only a portion of the monomeric alkylsilane is added initially, the reaction mixture may be heated prior to the addition of the catalyst, followed by the later edition of the remaining alkylsilane. Preferably all reactants, including the catalysts, are added simultaneously, and the reaction mixture subsequently heated. However, one skilled in the art will recognize that the reaction conditions based on this disclosure may be adjusted or varied depending on the selected starting materials, reaction conditions, reagents, and catalysts selected.

Once the trialkylsilane of the invention is formed, it may be used in various chromatographic applications, including reverse phase HPLC applications. The trialkylsilanes, preferably having at least one hydrolyzable group bound to the silicon in the terminal silyl moiety, may be used to treat substrates comprising, for example, silicon, preferably those containing materials such as silica. The substrates containing silicon atoms may be treated by suspending or dispersing the substrate material in a solvent or in another liquid medium. If silica is used, it is preferred that the silica is relatively dry. The trialkylsilane is added to the silica/liquid medium, and the silica and the trialkylsilane are reacted in the presence of an amine such as, for example, pyridine, in order to initiate reaction with a hydroxyl-containing support, such as silica. The resultant Si—O—Si bond provides a point of attachment between the substrate and the trialkylsilane of the invention. Specific reaction mechanisms which may be used for attaching the branched alkylsilanes of the invention to silica to form a treated substrate are described in, for example, P. Van Der Voort et al., J. Liq. Chrom. and Rel. Technol., 19 (17 and 18), p. 2743–52 (1996), the contents of which are incorporated herein by reference.

The reactions used to attach the trialkylsilane of the invention to a substrate may be modified in accordance with the substrate type used or the specific trialkylsilyl or silyl moieties involved. However, it is preferred that the hydrolyzable groups bound to the silicon atom in the terminal silyl moiety be capable of reacting with a hydroxy group in order to allow for an oxygen attached to a silicon atom to form a link to the substrate. The treated substrate having the trialkylsilane attached to the substrate surface as described above may be used as a bonded phase in chromatographic applications.

A bonded phase may be formed, for example, by preparing a trialkylsilane in accordance with the invention, and reacting it with a substrate comprising silicon in the presence of a hydroxy-containing compound to form an Si—O—Si bond between the silicon of the silyl moiety and the silicon of the substrate as described above. Once the treated substrate is formed, it must be separated from the solvent or other liquid medium for use as a bonded phase. Any separation technique may be used as is known or to be developed in the art, such as filtering.

The trialkylsilanes of the present invention are good bonding phases for use in reverse-phase HPLC applications. They show good separation characteristics for both hydrophobic and hydrophilic mixtures, robust stability, and no tendency towards phase collapse (the folding phenomenon observed in prior art compounds).

EXAMPLE 1

Prior to preparing the trialkylsilane of the invention, a disubstituted vinylsilane was prepared. The disubstituted vinylsilane prepared was di-n-octylmethylvinylsilane. A 5-L flask equipped with mechanical stirrer, condenser, and pot thermometer was charged with 150.60 g (6.19 mol) of magnesium turnings. After gently heating the reaction flask with a mantle for 30 minutes under a flow of dry nitrogen gas 0.5 L of tetrahydrofuran (THF) was added followed by the addition of 65.8 g (0.44 mol) of 1-chlorooctane and a small amount of iodine. After initiation of the reaction 1.5L of THF was added followed by the dropwise addition of 811.4 g (5.46 mol) 1-chlorooctane at such rate as to maintain a gentle reflux of the reaction mixture. After the addition was complete the reaction mixture was heated to reflux for 3 h followed by the dropwise addition of 332.9 g (1.09 mol) of vinylmethyldichlorosilane over a period of 1.5 h. After the addition was complete the reaction mixture was heated at reflux for 2 h, after which time gas chromatographic (GC) analysis showed all of the vinylmethyldichlorosilane to be reacted. The organic layer was washed with water (2×1L) and dried over sodium sulfate. Evaporation of the solvent provided 648.0 g (93.8% based on 90% purity) of the title compound. This material of was found to be suitable in the preparation of the trialkylsilanes of the invention.

EXAMPLE 2

A trialkylsilane of the invention was prepared. The trialkylsilane prepared was di-n-octylmethyl(2-trichlorosilylethyl)silane. A 500 mL flask equipped with magnetic stirrer, condenser, and addition funnel was charged with 243.9 g (0.75 mol based on 90% purity) of di-n-octylmethylvinylsilane from Example 1. The flask was warmed to 80° C. and 0.5 mL of chloroplatinic acid in THF was added followed by the addition of 15 mL (0.15 mol) of trichlorosilane. The temperature increased to 96° C. An additional 60 mL (0.61 mol) of trichlorosilane was added over a 30 min period during which time the reaction temperature reached a high of 146° C. The reaction mixture heated for 45 min at 110° C. after which time GC analysis showed no starting vinylsilane remaining. Distillation provided 244.0 g (76%) of the trialkylsilane compound. The di-n-octylmethyl(2-trichlorosilylethyl)silane thusly prepared made an excellent bonding phase for use in reverse phase HPLC applications, and exhibited good separation characteristics for both hydrophobic and hydrophilic mixtures and no tendency towards phase collapse.

EXAMPLE 3

A trialkylsilane of the invention was prepared. The trialkylsilane prepared was di-n-octylmethyl(2-dimethylchlorosilylethyl)silane. A 500 mL flask equipped with magnetic stirrer, condenser, and addition funnel was charged with 243.9 g (0.75 mol based on 90% purity) of di-n-octylmethylvinylsilane from Example 1. The flask was warmed to 80° C. and 0.5 mL of chloroplatinic acid in THF was followed by the addition of 15 mL (0.14 mol) of dimethylchlorosilane. The temperature increased to 102° C. An additional 170.8 mL (0.61 mol) of dimethylchlorosilane was added over a 30 min period during which time the reaction temperature reached a high of 142° C. The reaction mixture heated for 45 min at 100° C. after which time GC analysis showed no starting vinylsilane remaining. Distillation provided 247.0 g (85%) of the trialkylsilane compound. The di-n-octylmethyl(2-dimethylchlorosilylethyl)silane prepared exhibited good separation characteristics for hydrophobic and hydrophilic mixtures, and exhibited no tendency towards phase collapse.

EXAMPLE 4

A trialkylsilane in accordance with the invention was prepared. The trialkylsilane was di-n-dodecylmethylvinylsilane. First, a disubstituted vinylsilane was prepared as follows. A 5-L flask equipped with mechanical stirrer, condenser, addition funnel, and pot thermometer was charged with 99.7 g (4.10 mol) of magnesium turnings. After gently heating the reaction flask with a mantle for 30 minutes under a flow of dry nitrogen gas 0.5 L of diethyl ether was added followed by the addition of 25 g (0.10 mol) of 1-bromododecane and a small amount of iodine. After initiation of the reaction 1.5 L of diethyl ether was added followed by the dropwise addition of 996.96 g (4.00 mol) 1-bromdodecane at such as rate as to maintain a gentle reflux of the reaction mixture. After the addition was complete the reaction mixture was heated to reflux for 3 h followed by the dropwise addition of 220.8 g (1.75 mol) of vinylmethyldichlorosilane in 300 ml of diethyl ether over a period of 1.5 h. After the addition was complete the reaction mixture was stirred at room temperature for 14 h after which time GC analysis showed all of the vinylmethyldichlorosilane to be reacted. The reaction mixture was filtered and the salts washed with anhyrous diethyl ether (2×250 mL). The mixture was concentrated at 60° C. and 2 mm Hg to give 374.0 g of a viscous residue, which was greater than 87% of the desired intermediate.

To accomplish the hydrosilation reaction which resulted in the trialkylsilane of the invention, the residue was heated to 80° C. and 40 g (0.30 mol) of trichlorosilane was added followed by the addition of 1.0 mL of chloroplatinic acid. The reaction mixture was heated to 105° C. and 196.4 g (1.45 mol) of trichlorosilane was slowly added. After the addition was complete the reaction mixture was heated at 100° C. for 2 h. Distillation at atmospheric pressure gave 479 g (50%) of the desired product, bp 245–250° C./1 mm Hg. When used as a bonded phase, the resultant trialkylsilane exhibited good separation characteristics and no tendency towards phase collapse and the concomitant loss of resolution in performance, when used in chromatographic applications.

EXAMPLE 5

A trialkylsilane of the invention was prepared. The trialkylsilane was di-n-octylmethyl(2-trichlorosilylethyl)silane. A 500 mL flask equipped with magnetic stirrer, condenser and addition funnel was charged with 187 g (0.68 mol based on 87% purity) of di-n-octylmethylvinylsilane from Example 1. The flask was warmed to 80° C. and 0.5 mL of chloroplatinic acid in THF was added followed by the addition of 30 mL (0.3 mol) of trichlorosilane. The temperature increased to 124° C. An additional 50 mL (0.5 mol) of trichlorosilane was added over a 30 min period during which time the reaction temperature reached a high of 136° C. The reaction mixture heated for 45 min at 110° C. after which time GC analysis showed no starting vinylsilane remaining. Distillation provided 182 g (76%) of the compound. The resultant trialkylsilane was suitable for use in chromatographic applications and exhibited good separation characteristics, retention times, and no tendency towards phase collapse.

EXAMPLE 6

A trialkylsilane of the invention was prepared. The trialkylsilane was di-n-dodecylmethyl(2- dimethylchlorosilylethyl)silane. A 500 mL flask equipped with magnetic stirrer, condenser, and addition funnel was charged with 187 g (0.68 mol based on 87% purity) of di-n-octylmethylvinylsilane from Example 1. The flask was warmed to 80° C. and 0.5 mL of chloroplatinic acid in THF was added followed by the addition of 30 mL (0.3 mol) of dimethylchlorosilane. The temperature increased to 118° C. An additional 60 mL (0.6 mol) of dimethylchlorosilane was added over a 30 min period during which time the reaction temperature reached a high of 148° C. The reaction mixture heated for 45 min at 100° C. after which time GC analysis showed no starting vinylsilane remaining. Distillation provided g (85%) of the compound. The resultant trialkylsilane exhibited good separation techniques and no tendency towards phase collapse.

EXAMPLE 7

A treated substrate for use in chromatographic applications was prepared, bonding a trialkylsilane of the invention with a silica substrate. The trialkylsilane of the invention was di-n-dodecylcylmethylsilyethyl) silane. A 1-L 3-neck round bottom flask equipped with mechanical stirrer, condenser and pot thermometer was charged with 300 mL of toluene and 32.0 g of Kromasil 60A, 5u spherical silica. The silica was dried by azeotropic distillation. 12 mL of pyridine and 25 g of di-n-dodecylmethyl(2-trichlorosilylethyl)silane were added to the dried silica mixture. The mixture was refluxed (114° C.) with mechanical stirring for 4 hrs. After the reaction mixture had cooled to 50° C., 4.4 mL of pyridine and 6.6 g of isopropyldimethylchlorosilane were added. The mixture was refluxed for 15 hrs. with mechanical stirring. The reaction mixture after cooling to room temperature was transferred to a 800 mL beaker containing 300 mL of methyl alcohol. The mixture was filtered through a 15.0 cm Buchner funnel fitted with two pieces of Whatman #5 filter paper (2.5 micron porosity), washed with 500 ml of methyl alcohol and air dried for 10 hours. The air dried bonded silica was transferred to a 1-L round bottom flask containing 500 mL of tetrahydrofuran, refluxed with mechanical stirring for 6 hours and filtered through a 15.0 cm Buchner funnel fitted with 2 sheets of Whatman #5 paper. The bonded silica cake was washed with 500 mL of methyl alcohol, air dried for 10 hours, and transferred to a drying dish for drying in a convection oven at 110° C. for 6 hours. The di-n-dodecylmethylsilylethyl bonded silica had a carbon analysis of 17%, and was suitable for chromatographic applications.

EXAMPLE 8

The di-n-dodecyl(methylsilyl) bonded silica of Example 7 was evaluated in a chromatographic application. Polar compounds that are low molecular weight carboxylic acids were run on the column in a straight (100%) aqueous mobile phase. The carboxylic acids selected for the analysis were acetic acid, ascorbic acid, citric acid, formic acid, oxalic acid, and tartaric acid. The column was a 250×4.6 mm stainless steel HPLC column that was packed with a 60 Å, 5 µÅ di-n-dodecyl methylsilylethyl bonded silica phase by conventional packing methodology. The mobile phase used was 0.05 M $KH_2PO_4$ at pH 2.4. Flow rate was 1 ml/minute, detection was 220 nm and the injection sample size was 10 ul. As a control, the identical carboxylic acid solvent was run under identical conditions, but using a conventional column consisting of convention C18 bonded silica. A separation of the carboxylic acid compounds on the di-n-dodecylmethylsilylethyl bonded silica column of the invention is shown in FIG. 3.

EXAMPLE 9

A retention stability study using a di-n-dodecylmethylsilylethyl bonded silica column and a conventional C18 column, each prepared as in Example 8, was carried out, using citric acid or carboxylic acids, including citric acid, as the test probe. Each of the chromatographic runs was carried out as in Example 8 (mobile phase 0.05M $KH_2PO_4$ at pH 2.4; flow rate 1 mL/minute; detection 220 nm; injection sample size 10 µl).

The results of each run are shown in FIG. 4 (citric acid on column of the invention) and FIG. 5 (carboxylic acids including citric acid on C18 column). After two hundred hours (200) of continuous elution with a 0.05 M $KH_2PO_4$, pH 2.3 mobile phase, the column of the invention showed no loss in retention of the citric acid (FIG. 4). In contrast, a complete loss of retention was shown after mere fifteen (15) hours of continuous elution using the conventional column (FIG. 5).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of preparing a trialkylsilane for use in chromatographic applications, the method comprising:
   (a) preparing a disubstituted vinylsilane by reacting an organomagnesium reagent and a vinylfunctional silane;
   (b) reacting the disubstituted vinylsilane of step (a) and a monomeric silane containing a silicon-hydrogen bond in the presence of a metallic catalyst, such that the monomeric silane is added to a vinyl group of the vinylsilane, thereby binding the silicon of the monomeric silane to a terminal carbon of the vinyl group and forming a trialkylsilane having a terminal trialkylsilyl moiety, wherein at least two alkyl groups of the trialkylsilyl moiety independently comprise at least six carbons atoms and the at least two alkyl groups extend from a silicon of the prepared disubstituted vinylsilane of step (a).

2. The method of claim 1, wherein the vinylfunctional silane of step (a) is an alkyl vinylfunctional silane.

3. The method of claim 1, wherein the vinylfunctional silane of step (a) is an aryl vinylfunctional silane.

4. The method of claim 1, further comprising providing at least one hydrolyzable group to the monomeric silane, such that the resulting trialkylsilane comprises at least one hydrolyzable group for use in binding the trialkylsilane to a substrate.

5. The method of claim 1, wherein the at least one hydrolyzable group is selected from the group consisting of a halogen, an alkylamine group, a dialkylamine group, and an alkoxy group.

6. The method of claim 5, wherein the hydrolyzable group is selected from the group consisting of chlorine and dimethylamine.

7. The method of claim 1, wherein the trialkylsilane is a dialkylmethylsilylethylsilane.

8. The method of claim 1, wherein the metallic catalyst of step (b) is selected from the group consisting of platinum-divinyltetramethyldisiloxane complex, platinum-cyclovinylmethylsiloxane complex, chloroplatinic acid, chloroplatinic acid complexes, chloroplatinic acid solutions, and tris-triphenyl phosphine rhodium chloride.

9. A method for forming a bonded phase for use in chromatographic applications, the method comprising:
(a) forming a trialkylsilane comprising a hydrocarbon backbone having one to ten carbon atoms; a terminal trialkylsilyl moiety on the hydrocarbon backbone, wherein at least two of the alkyl groups of the trialkylsilyl moiety independently comprise six to eighteen carbon atoms; a terminal silyl moiety on the hydrocarbon backbone, wherein the silicon of the silyl moiety is capable of being bound to a substrate, and
(b) reacting the trialkylsilane of step (a) with the substrate comprising silicon in the presence of a hydroxy-containing compound to form a Si—O—Si bond between the silicon of the silyl moiety and the silicon of the substrate, such that the at least two alkyl groups of the trialkylsilyl moiety extend to provide a bonded phase useful for reproducible molecular interaction.

10. The method of claim 9, wherein step (b) further comprises reacting the trialkylsilane and substrate in a solvent solution and wherein the method further comprises separating the substrate from the solvent solution.

* * * * *